United States Patent [19]
Stanley

[11] Patent Number: 5,557,007
[45] Date of Patent: Sep. 17, 1996

[54] UNSATURATED POLYLACTONE ACRYLATES AND DERIVATIVES THEREOF

[75] Inventor: James P. Stanley, Bound Brook, N.J.

[73] Assignee: Union Carbide Chemicals & Plastics Technology Corporation, Danbury, Conn.

[21] Appl. No.: 591,445

[22] Filed: Sep. 28, 1990

[51] Int. Cl.$^6$ .......................... C07C 69/757; C08F 32/00
[52] U.S. Cl. .......................... 560/183; 522/182; 526/309; 560/128; 560/185; 560/193; 560/217; 560/220
[58] Field of Search .................................. 560/193, 217, 560/220, 185, 128, 183; 522/182; 526/309

[56] References Cited

U.S. PATENT DOCUMENTS

| Re. 29,131 | 2/1977 | Smith et al. | 260/77.5 AN |
|---|---|---|---|
| 3,536,687 | 10/1970 | Nordstrom | 260/89.5 |

FOREIGN PATENT DOCUMENTS

| 0435265 | 3/1991 | European Pat. Off. . | |
| 0193945 | 10/1985 | Japan | 560/220 |
| 8701697 | 3/1987 | WIPO | 560/220 |

OTHER PUBLICATIONS

Frostick et al., JACS, 81, 3350 (1959).
CA 55: 14983e (1959).
CA 111 (20): 174832g (1989).
CA 112 (8): 56951j (1989).
CA 112 (24): 218938q (1990).
CA 110 (10): 77623c (1988).
CA 112 (22): 200731g (1989).
CA 97 (6): 40442e (1982).

*Primary Examiner*—Gary Geist
*Assistant Examiner*—B. Frazier
*Attorney, Agent, or Firm*—W. K. Volles

[57] ABSTRACT

Novel unsaturated polylactone acrylates are produced by the reaction of an unsaturated polylactone, such as that produced in the reaction of a lactone with tetrahydrobenzyl alcohol, and a lower-alkyl acrylate under transesterification conditions. The unsaturated polylactone acrylate product may be subsequently epoxidized to form novel 3,4-epoxy polylactone acrylates.

19 Claims, No Drawings

és,557,007

UNSATURATED POLYLACTONE ACRYLATES AND DERIVATIVES THEREOF

BACKGROUND OF THE INVENTION

1. Field of the Invention

This invention deals with compounds that combine either a precursor to a cycloaliphatic epoxide, a lactone, and an acrylate or a cycloaliphatic epoxide, a lactone, and an acrylate to form novel compounds that are useful as intermediates in various ways including coatings, inks, adhesives, sealants, shaped articles, and other end uses.

2. Description of the Prior Art

Cycloaliphatic epoxides, poly-ε-caprolactone polyols, and acrylates are all known materials that are useful in the arts of coatings, inks, adhesives, sealants, and forming shaped articles. Cycloaliphatic epoxides and acrylates are useful, for example, in making products with high performance characteristics that can withstand weathering. Poly-ε-caprolactone polyols are known to provide flexibility and/or toughness to a variety of products. The products are usually formed by opening of the oxirane ring on the cycloaliphatic epoxide, by reaction of the ethylenic unsaturation in the acrylate, and by reaction of the hydroxyl end-groups of the poly-ε-caprolactone polyols.

Unsaturated polylactone derivatives of the following structural formula are known:

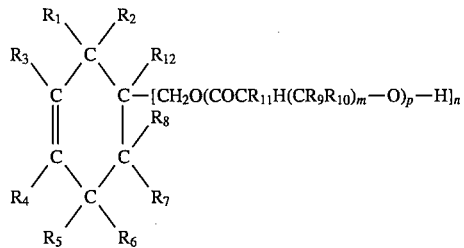

wherein $R_1$ through $R_8$ are the same or different and are hydrogen, phenyl, or unsubstituted or substituted alkyl groups of 1 to about 8 carbon atoms, n has a value of one or two, $R_{12}$ is hydrogen when n is one and does not exist when n is two, $R_9$ through $R_{11}$ are the same or different and are hydrogen, phenyl, or lower alkyl having 1 to about 5 carbon atoms with the proviso that not more than three of the $R_9$ through $R_{11}$ groups are alkyl or phenyl groups, m is an integer of from zero to about 12, and the average value of p has a value of from zero to about 30 or more. Also known are the 3,4-epoxides of such compounds and other derivatives prepared by coupling two of more of these molecules. Such compounds are disclosed in U.S. patent application Ser. No. 07/457,922, filed on Dec. 27, 1989, now abandoned, the disclosure of which is incorporated herein by reference.

Cyclohexenyl-alkyl and alkylcyclohexenyl-alkyl alcohol esters of α,β-unsaturated acids as well as their homopolymers and copolymers are described in U.S. Pat. No. 3,536, 687. The structural form of the monomer used was as follows:

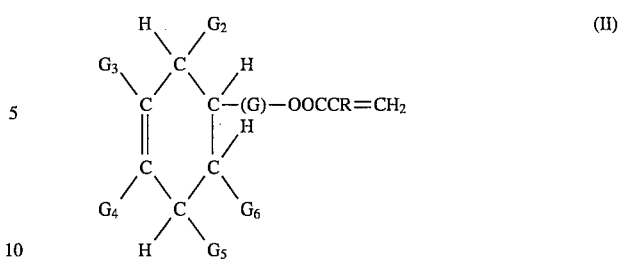

wherein R is hydrogen or methyl, G is alkyl and preferably lower alkyl having 1 to 4 carbon atoms, and $G_2$ to $G_6$ are hydrogen, alkyl, halogen, or alkoxy. These monomers were polymerized into soluble polymers that were used to make coatings. The coatings were oxidatively crosslinked in air and thus rendered insoluble.

(3,4-Epoxycyclohexyl)methyl acrylate and 3,4-epoxy-6-methylcyclohexyl)methyl acrylate have been described by Frostick and coworkers in J. American Chemical Soc., 81, 3350 (1959). Methacrylates of 3,4-epoxycyclohexanemethanols, which may be substituted with alkyl groups of up to 12 carbon atoms, especially with methyl in the 6-carbon position, are described in German Patent 1,063, 808, Aug. 20, 1959 (Chemical Abstracts 55:14983e). These compounds were polymerized alone or together with olefinic compounds and subsequently hardened by reaction of the epoxide group.

Also known are compounds such as

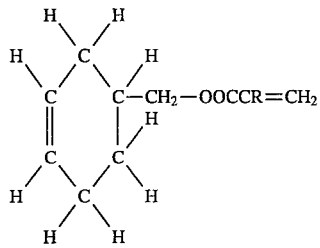

and

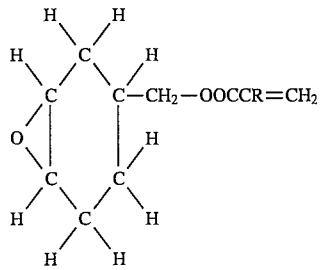

wherein R is hydrogen or methyl. These compounds are described in Japanese patent applications J01096177-A, published Apr. 14, 1989 (Chemical Abstracts 111(20):174832y) and J01186876-A, published Jul. 26, 1989 (Chemical Abstracts 112(8):56951j).

Japanese patent application 02018410, published Jan. 22, 1990 (Chemical Abstracts 112(24):218938q) describes the preparation of coatings for erasable white boards by curing siloxane methacrylates with (3,4-epoxycyclohexyl)methyl methacrylate. German Offenlegungsschrift DE-3807571, published Sep. 22, 1988 (Chemical Abstracts 110(10):77623c) deals with copolymers from the same monomers. German Offenlegungsschrift DE-3916035-A, published Nov. 30, 1989 (Chemical Abstracts 112(22):200731g) is a description of the reaction products of vinyl resins bearing acid groups and unsaturated alicyclic epoxides including (3,4-epoxycyclohexyl)methyl methacrylate. Copolymers containing (3,4-epoxycyclohexyl)methyl acrylate or methacrylate are described in a Japanese patent application J57047365-A, published Mar. 18, 1982 (Chemical Abstracts 97(6):40442e) as useful in thermosetting powder coating compositions.

However, not previously suggested or disclosed are the novel unsaturated polylactone acrylate, methacrylate, or ethacrylate derivatives and epoxidized polylactone acrylate, methacrylate, or ethacrylate derivatives of this invention, their derivatives, and their range of useful properties.

SUMMARY OF THE INVENTION

The novel polylactone acrylate compounds of this invention are those defined by the following structural formulas. The unsaturated polylactone acrylate compounds are described by structural formula V:

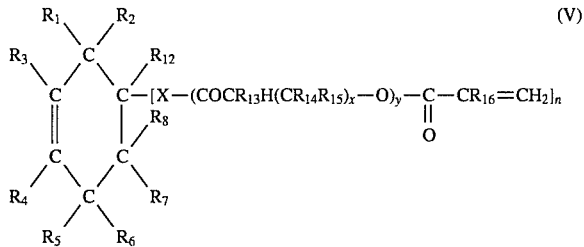

wherein $R_1$ to $R_8$ are the same or different and are hydrogen, phenyl, or unsubstituted or substituted alkyl groups of 1 to about 8 carbon atoms, n has a value of one or two, $R_{12}$ is hydrogen when n is one and does not exist when is two, $R_{13}$ to $R_{15}$ are the same or different and are hydrogen, phenyl, cyclohexyl, linear or branched alkyl groups of up to about 8 carbon atoms, or halogen with the proviso that not more than three of the $R_{13}$ to $R_{15}$ are alkyl, phenyl, cyclohexyl, or halogen groups, $R_{16}$ is hydrogen, methyl, or ethyl, x is an integer of one to about 6, and the average value of y is from about 0.1 to about 50, preferably from about 0.1 to about 10, and most preferably from about 0.1 to about 4, X is $CH_2O$ when n is equal to two and is $CH_2O$ or $COOCH_2CHR_{17}O$ when n is equal to one, and $R_{17}$ is either hydrogen or methyl. It is preferred that at least one of $R_3$ or $R_4$ be hydrogen, and it is most preferred that both $R_3$ and $R_4$ be hydrogen.

The novel epoxy polylactone acrylates of this invention are those defined by structural formula VI:

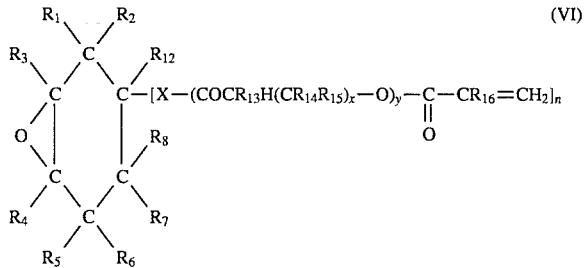

wherein $R_1$ through $R_8$, $R_{12}$ through $R_{16}$, x, y, and n are as described above.

The cycloaliphatic epoxide acrylate molecules have a combination of polymerizable acrylate groups that can be cured with free radicals and epoxide groups that can be cured with Bronsted or protonic acids or with Lewis acids. In addition, the epoxide and acrylate functionality are connected by flexible, variable length lactone molecule bridges that provide for flexibility, adhesion, and toughness.

When either homopolymerized or copolymerized, the above-described compounds are useful in a variety of ways, including as components or sole reactive vehicles of coatings, adhesives, inks, and sealants; as acid scavengers; as flame retardants after reaction with halogens and/or phosphorous compounds; molded or cast objects; and as intermediates to preparation of other compounds useful in diverse end uses, including as inert solvents when hydrogenated or halogenated, as pharmaceuticals and medical products. Illustrative of such product applications are furniture coatings, decorative coatings, electrical or electronic coatings; automobile primers, sealers, and topcoats; tough automobile rocker panel coatings; beverage can coatings and can-end coatings; inks for written or pictorial communication; sealants for electronic components; stereolithography materials; and the like. The coatings, inks, sealants, and adhesives can be applied by a number of conventional techniques, illustrative of which are spray, brush, or roll coating, screen printing, lithography, bulk dispensing, and the like, and can be cured by a variety of techniques, including exposure to thermal energy, actinic radiation such as visible light, ultraviolet light, electron beams, and x-rays, and the like.

DETAILED DESCRIPTION OF THE INVENTION

The Unsaturated Polylactone Acrylates

The novel unsaturated polylactone acrylates (V) of this invention are produced by a transesterification reaction between a lower alkyl acrylate, methacrylate, or ethacrylate, VII, and an unsaturated polylactone, VIII,

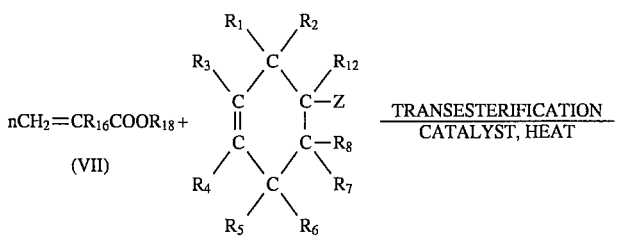

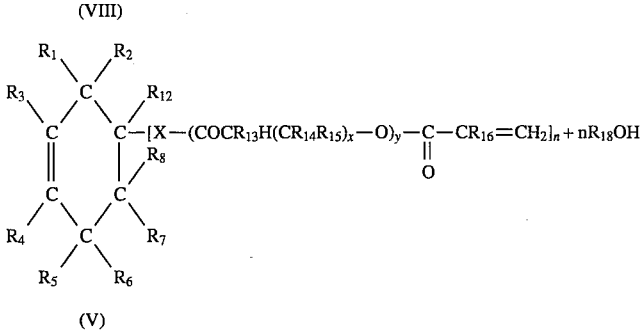

wherein Z is $[X-(COCR_{13}H(CR_{14}R_{15})_x-O)_y-H]_n$, $R_1$ to $R_{16}$, x, y and n are as defined above, and $R_{18}$ is linear or branched lower alkyl of one to about eight carbon atoms and preferably one to about four carbon atoms. Illustrative of linear or branched lower alkyl groups are methyl, ethyl, n-propyl, i-propyl, n-butyl, i-butyl, s-butyl, t-butyl, 2-methyl-1-propyl, 1,2-dimethyl-1-propyl, 2-methyl-1-butyl, n-amyl, i-amyl, 3-methyl-pentyl, n-hexyl, 2-methyl-1-pentyl, 3-methyl-1-pentyl, 2-ethyl-hexyl, and the like. The term acrylate will be taken to include acrylates, methacrylates, and ethacrylates unless a specific acrylate is being discussed.

The lactones suitable for preparation of the unsaturated polylactones, I, and the 3,4-epoxides of these compounds are cyclic ester compounds of the general structure

where $R_{13}$ to $R_{15}$ have been defined above, with the proviso that not more than three of these R groups are alkyl, phenyl, cyclohexyl, or halogen groups, preferably that not more than two of these R groups are alkyl, phenyl, cyclohexyl, or halogen groups, and most preferably that all of these R groups are hydrogen; that x is an integer of one to about 6, preferably from 3 to 5, and most preferably 4. Illustrative of the lactones that can be used are e-caprolactone, 3,5-dimethyl-e-caprolactone, e-methyl-e-caprolactone, ö-isopropyl-e-caprolactone, e-phenyl-a-methyl-e-caprolactone, w-valerolactone, w-methyl-w-valerolactone, ö-propriolactone, zeta-enantholactone, and the like, as well as mixtures of these lactones. The most preferred lactone is e-caprolactone.

The group X in structural formulas V and VI, as well in later structural formulas, is $CH_2O$ when n is equal to two and is $CH_2O$ or $COOCH_2CHR_{17}O$ when n is equal to one. Illustrative of the compounds with group X that can be reacted with lactones to obtain the unsaturated polylactones used in the practice of this invention include 3-cyclohexene-1,1-dimethanol,

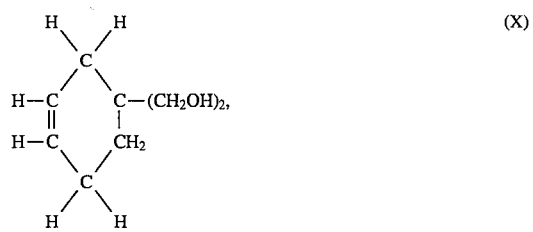

3-cyclohexene-3-methyl-1,1-dimethanol,

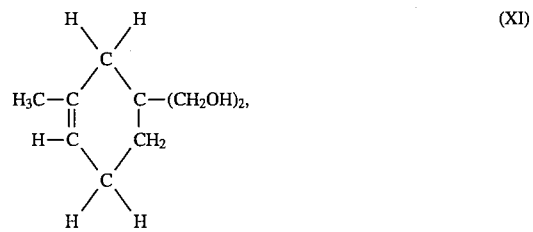

3-cyclohexene-4-methyl-1,1-dimethanol,

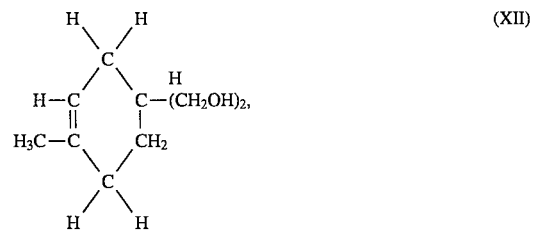

when n equals two and, when n equals one,
3-cyclohexene-1-methanol,

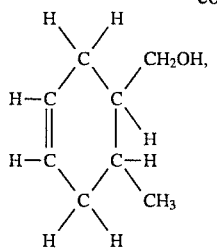

3-cyclohexene-6-methyl-1-methanol,

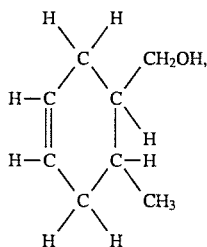

hydroxyethyl-3-cyclohexene carboxylate,

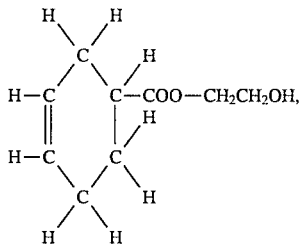

hydroxyethyl-3-cyclohexene-6-methyl carboxylate,

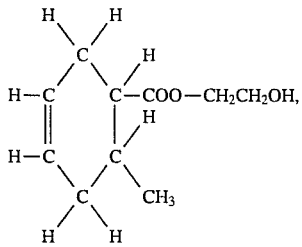

hydroxypropyl-3-cyclohexene-6-methyl carboxylate,

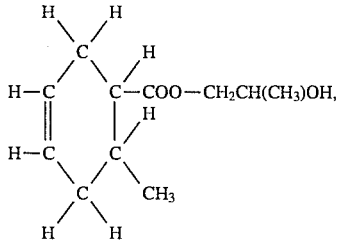

hydroxypropyl-3-cyclohexene carboxylate,

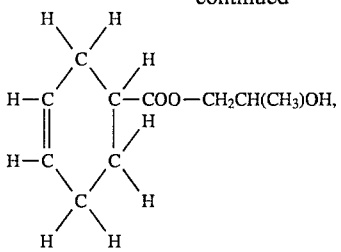

hydroxyethyl-3-cyclohexene-3-methyl carboxylate,
hydroxyethyl-3-cyclohexene-4-methyl carboxylate,
hydroxyethyl-3-cyclohexene-3,6-dimethyl carboxylate,
hydroxypropyl-3-cyclohexene-3-methyl carboxylate,
hydroxypropyl-3-cyclohexene-4-methyl carboxylate,
hydroxypropyl-3-cyclohexene-4,6-dimethyl carboxylate,
and the like.

The transesterification process can be carried out with either an unsaturated polylactone or a 3,4-epoxy polylactone; however, it is preferred that unsaturated polylactones be used and that when a 3,4-epoxy polylactone is used the average value of y be less than about 1.2.

The transesterification process can be carried out with an excess of the unsaturated polylactone or epoxidized polylactone, an equivalent amount of the reactants, or an excess by weight of from about 5% to 400% or more of the lower-alkyl acrylate be used. It is usually preferred that an excess of the lower-alkyl acrylate be used to facilitate rapid, efficient reaction between the compounds when a fully acrylated product is prepared. Although residual lower-alkyl acrylate can be allowed to remain in the final product wherein it would act as a reactive diluent, it is preferably removed by distillation or other suitable separation technique.

Although it is preferred that the transesterification process is practiced with both the unsaturated polylactones and the 3,4-epoxy polylactones, it is realized that a condensation process between an unsaturated polylactone and acrylic, methacrylic, or ethacrylic acid could be used to make the unsaturated polylactone acrylates, V, of the invention and that these compounds can be epoxidized to form the 3,4-epoxy polylactone acrylates, VI, of the invention.

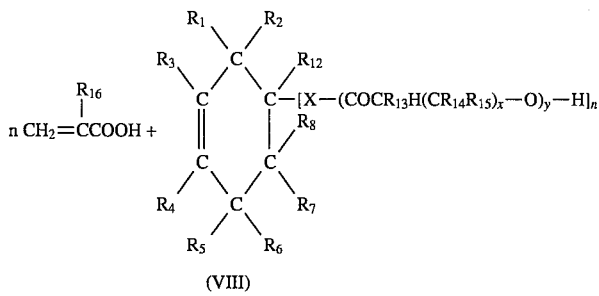

(VIII)

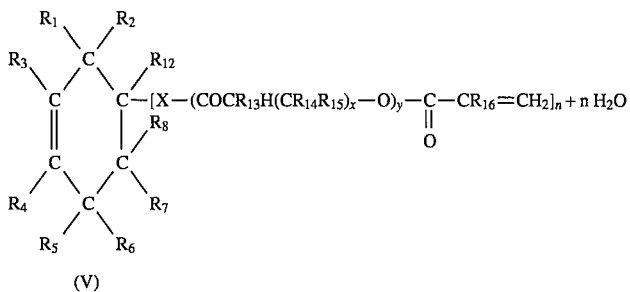

(V)

Illustrative of the catalysts for the transesterification reaction are metallic methoxides such as sodium methoxide, potassium methoxide, lithium methoxide, zinc methoxide, calcium methoxide, cesium methoxide; metallic bicarbonates such as sodium bicarbonate, potassium bicarbonate; sodium carbonate, potassium carbonate; sodium thiocyanate, potassium thiocyanate, lithium thiocyanate, cesium thiocyanate, zinc thiocyanate; potassium cyanide, sodium cyanide; and other salts of weak acids such as sodium acetate, lithium acetate, potassium acetate, cesium acetate, calcium acetate, zinc acetate, calcium oxide, calcium hydride, metal oxylates, and the like. In addition, mixtures of the catalysts can be used when desired. When the 3,4-epoxy polylactones are employed, it is preferred that the salts of weak acids be employed. The catalyst may be added to the reaction mass all at one time, in discrete portions that may be of the same or different size, or in a continuous uniform or nonuniform manner over the entire reaction time period or over a portion of the reaction time period.

The transesterification reaction can be carried out at temperatures of about 40° C. to about 180° C. and preferably at temperatures of about 60° C. to about 130° C. The temperature involved will be dependant on the particular reactants used and particularly on the boiling point of the leaving alcohol. Time for completion of the transesterification reaction will vary depending on the temperature employed, the particular ingredients involved, and the quantity of ingredients used. The pressure employed during the transesterification process is not critical, and the process may be carried out under atmospheric pressure or subatmospheric pressure, or, less preferably, at superatmospheric pressure.

The mixture of reactants for the transesterification reaction can optionally be dissolved or suspended in an inert solvent for the purpose of facilitating the reaction, reducing the viscosity, or to facilitating handling. Illustrative of the inert solvents are ethyl benzene, toluene, xylene, benzene, trichloroethane, heptanone, methyl amyl ketone, hexane, heptane, and the like.

As is known to those skilled in the art of acrylate reactions, it is usually necessary to add inhibitors to the reaction mixture to prevent polymerization of the acrylate, methacrylate, or ethacrylate double bond during heating. Illustrative of such inhibitors are methoxyphenol, phenothiazine, benzoquinone, 2,5-di-t-butylquinone, methylhydroquinone, hydroquinone, other common free radical inhibitors, and the like. The level of inhibitor used is less than 2000 parts per million and preferably less than 1000 parts per million.

In a specific embodiment of this invention, the unsaturated polylactone acrylates of this invention can be made into 3,4-epoxy polylactone acrylates by reaction with a suitable oxidizing agent such as peracetic acid.

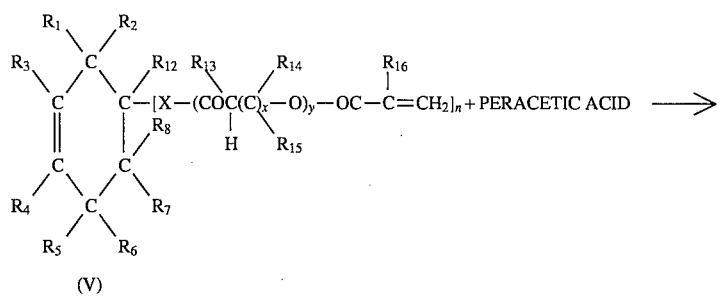

(V)

-continued

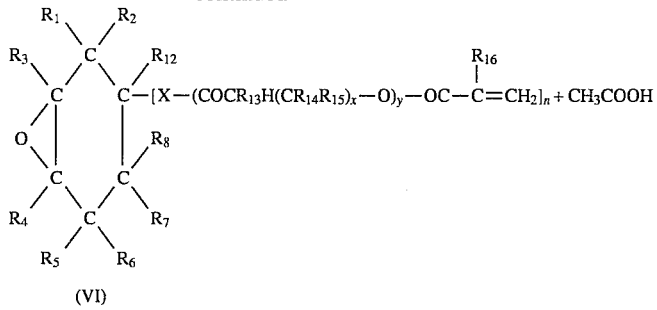

(VI)

To carry out the epoxidization, epoxidizing agents of various types can be used. These agents can be formed in situ from hydrogen peroxide and an organic acid such as acetic acid, can be preformed and used as a peracid, or can be in the form of a dioxirane such as dimethyldioxirane, and the like. Illustrative of the peracids that can be used in carrying out epoxidations are perbenzoic acid, peracetic acid, perpropionic acid, perbutyric acid, percaproic acid, perlactic acid, permonochloroacetic acid, permonosuccinic acid, tertiary-butylperbenzoic acid, and the like. When used, the peracids are usually dissolved in an inert solvent such as ethyl acetate to facilitate handling and to minimize explosive and other hazards.

The unsaturated polylactone acrylate derivative is reacted with the epoxidizing agent at temperatures of less than about 5° C. to about 90° C., preferably at temperatures of about 25° C. to 60° C. The time required for reaction will vary depending upon the particular reactants charged and the temperature, facts which are well known to those skilled in the art of epoxidation chemistry. In general, the peracid solution is carefully and very slowly added to the reactor containing the unsaturated polylactone acrylate, in either a neat form or dissolved in a suitable inert solvent such as ethyl acetate, which is held at a relatively constant reaction temperature. Rate of peracid addition should be such that a desired maximum temperature is not exceeded. The exothermic oxidation reaction that takes place is controlled by cooling the reactants to the desired reaction temperature. Peracid addition rate is decreased or stopped if necessary to maintain temperature control. A method of quenching the reaction is usually made available and maintained as, for example, in the laboratory an ice/water bath is available. The reaction product is then optionally washed one or more times with water and/or an aqueous solution of sodium chloride, sodium bicarbonate, or similar salt. The product is isolated by vacuum stripping of the organic acid that is formed and the solvent that had been used to dissolve the unsaturated polylactone acrylate and/or peracetic acid. If desired, the product may be redissolved and reisolated by vacuum stripping using conventional techniques.

In specific embodiments of this invention, the unsaturated polylactone acrylates of this invention can be used as, e.g., reactive solvents, or can be reacted with hydrogen under low pressure to prepare compounds without unsaturation and useful as inert solvents. Also, the compounds of this invention can be reacted with halogens, to form flame-retardant additives that will be miscible with a variety of polymers and other compounds. In the case of the 3,4-epoxy polylactone derivatives that have been reacted with halogen, the potential for linking and attaching the compound to various substrates through the epoxide group exists.

The unsaturated polylactone acrylates and 3,4-epoxy polylactone acrylates of this invention can be homopolymerized, copolymerized, or further reacted with other compounds to form a variety of useful coatings, inks, adhesives, sealants, molded or cast shaped objects, and intermediates for further reaction or use. When these compounds are used in coatings, inks, sealants, adhesive, and molded parts, they impart improved flexibility and/or toughness, presumably due to the lactone moieties in the compounds, to the resulting product over that obtained with compounds known in the literature. In addition, in the case of the unsaturated polylactone acrylate derivatives, unsaturation of different reactivity, i.e., cyclohexene, which, for example, can be readily converted into epoxide functionality, and acrylate functionality, that can be readily polymerized by free radical chemistry through thermal or radiation means, is provided. In the case of the epoxidized polylactone acrylate derivatives, different functionalities, i.e., epoxide and acrylate, are provided in the same molecule and therefore reactivity with different classes of compounds is provided. For example, the epoxide portion can be cationically cured if formulated with a suitable cationic photoinitiator such as the sulfonium or iodonium salts and exposed to suitable ultraviolet light and the acrylate portion of the molecule can be polymerized if formulated with a photoinitiator that generates free radicals, such as 2,2-diacetophenone, and exposed to ultraviolet light.

Illustrative of the various end uses in which the compounds of this invention can be used are acid scavengers, furniture coatings, decorative coatings, overprint varnishes, electrical or electronic coatings, automobile primers, sealers, coatings for rocker panel, top coatings, beverage and other can coatings, inks for written or pictorial communication, sealants for electronic components, conformal coatings, photoresists suitable for developing printing plates or printed circuit boards, shaped articles such as those formed in stereolithography, cast printing rolls, molded objects such as those formed by bulk molding compounds or sheet molding compounds based on unsaturated polyesters and styrene and reinforced with glass, carbon, graphite or other fibers, solvents, flame retardants, and the like.

The following examples are illustrative of the present invention and are not intended as a limitation upon the scope thereof.

EXAMPLES

Example 1

(Describes preparation of an unsaturated polycaprolactone methacrylate derivative by transesterification of an unsaturated polycaprolactone derivative and methyl methacrylate.) To a reaction flask 157 grams (0.695 equivalent) of a dry, unsaturated polycaprolactone derivative as disclosed in the above-mentioned patent application Ser. No. 07/457,922, having the average structure

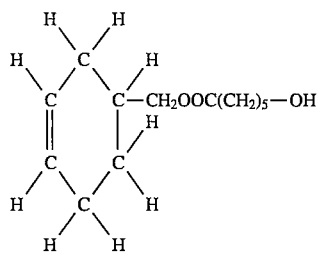

and an average molecular weight of about 226, 126 grams (1.248 equivalents) of dry methyl methacrylate, 42 grams of toluene, and 0.45 gram of methoxyphenol and 0.45 gram of phenothiazine were added and further dried by heating to 105° C. and distilling over about 15 cc of a mixture of water, toluene, and methyl methacrylate. The mixture was then cooled to room temperature and 0.45 gram of sodium methoxide was added. The reaction mixture was then heated to 105° C. while blowing a stream of nitrogen over the mixture. As methanol was produced in the reaction, it was distilled overhead along with some toluene and methyl methacrylate. As the reaction proceeded, the temperature of the reaction mixture was gradually increased to about 125° C. After about two hours, the reaction was terminated and the mixture was cooled to room temperature and the sodium methoxide was neutralized with an equal molar amount of acetic acid. The toluene and excess methyl methacrylate were stripped off under vacuum on a rotary evaporator to yield 191 grams of an unsaturated polylactone methacrylate of the following structure:

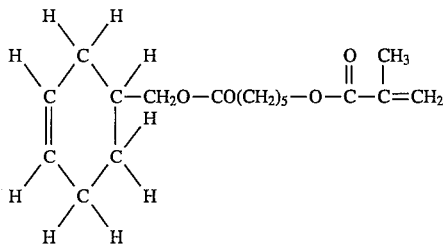

Example 2

(Describes the preparation of a 3,4-epoxy polycaprolactone methacrylate from an unsaturated polycaprolactone methacrylate.) One hundred and eight (108) grams of the unsaturated polylactone methacrylate prepared in Example 1 were placed in a reaction flask and heated to 35°–40° C. Then, 135 grams of a 23% peracetic acid in ethyl acetate solution were slowly added while stirring over a period of about one hour. The reaction temperature was controlled at 35°–40° C. by the rate of addition of the peracetic acid solution, an ice bath, and a heating lamp. After the peracetic acid solution addition was complete, the mixture was allowed to stir for an additional 2 to 3 hours at 35°–40° C. to ensure completion of the reaction. The reaction mixture was then cooled to room temperature and diluted with 100 grams of toluene, and washed 4 times with 120 milliliter portions of cold water, one time with cold, aqueous sodium bicarbonate solution, and three more times with water. The organic layer was then stripped of all volatile components at 45° C. using a rotary evaporator and an absolute pressure of 2 mm of mercury. There was a yield of 104 grams of the 3,4-epoxy polycaprolactone methacrylate of the following average structure:

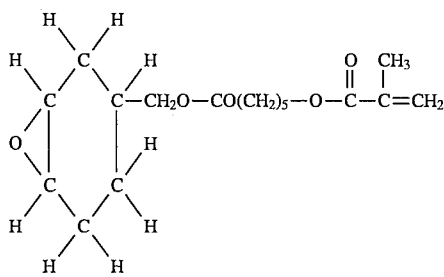

Example 3

To a reaction flask equipped with a distilling head, magnetic stirrer, heating mantle, and a slow nitrogen purge, 28 grams (0.08 mol) of an unsaturated polycaprolactone derivative having the average structure

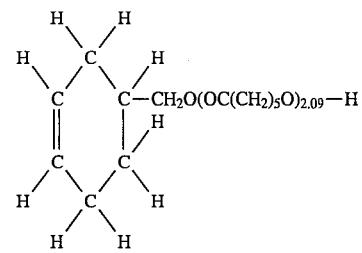

and an average molecular weight of 350, 24 grams (0.24 mol) of methyl methacrylate, 7 grams of toluene, and 0.1 g each of phenothiazine and methoxyphenol were added. The mixture was heated to boiling and 4–5 cc of a water-toluene azeotrope were collected through the distillation head. The mixture was then cooled to room temperature and 0.1 gram of sodium methoxide was added. Over the next 90 minutes, the reaction mixture was heated to between 100° C. and 123° C. and a mixture of methanol, toluene and excess methyl methacrylate was collected overhead at a distillation head temperature of 55°–65° C.

The cooled reaction mixture was then diluted with 50 cc of heptane, washed two times with 15 cc of water, one time with 15 ml portions of water that contained 0.2 gram of acetic acid and a final time with 15 cc of water. The organic layer was separated and stripped of all volatile compounds by distillation at a temperature of 50° C. and a pressure as low as 1 mmHg. The yield was 19 grams of unsaturated polycaprolactone methacrylate of the following average structure:

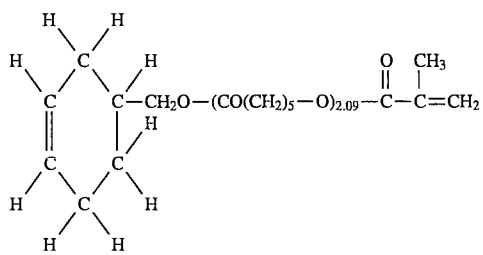

Example 4

In an apparatus similar to that described in Example 3, 125 grams (0.56 mol) of dried unsaturated caprolactone derivative having the average structure

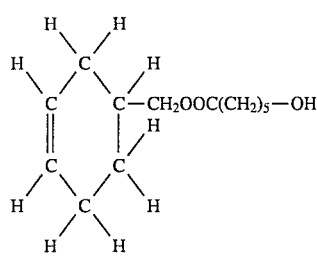

and an average molecular weight of 226, 100 grams (1.0 mol) of methyl methacrylate, 33 grams of toluene, and 0.36 gram each of phenothiazine and methoxyphenol were added. The mixture was heated to distill over about 15 cc of a water/toluene/methyl methacrylate mixture. The reaction mixture was then cooled to room temperature and 0.36 gram of sodium methoxide was added. The mixture was then heated to 100°–120° C. and held at this temperature while a mixture of methanol, toluene, and methyl methacrylate was distilled over at a head temperature of 55°–65° C. After cessation of distillation, the reaction product was cooled.

The reaction product was refined by neutralizing with 0.4 gram of acetic acid, diluting with 150 cc of toluene, and washing five times with 200 ml portions of water. The volatiles were stripped from the organic layer with a rotary evaporator at 45°–50° C. to yield 161 grams of an unsaturated caprolactone methacrylate with a number average molecular weight of 291 and of the following average structure:

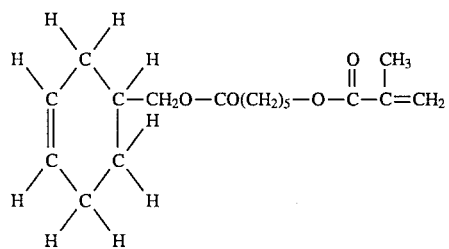

Example 5

The same ingredients in the same amounts as given in Example 4 were reached in the same manner as described in Example 4. After cooling the reaction mixture, it was refined by adding 0.4 gram of acetic acid and stripping off volatiles in a rotary evaporator at 45°–50° C. to yield 167 grams of an unsaturated caprolactone adduct of the following average structure:

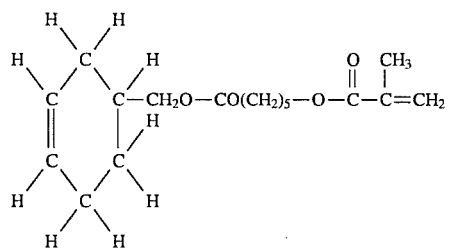

Example 6

To a reaction flask equipped as in Example 4, an addition funnel was also added. The reactor was charged with 125 grams (0.56 mol) of an unsaturated caprolactone derivative having the average structure:

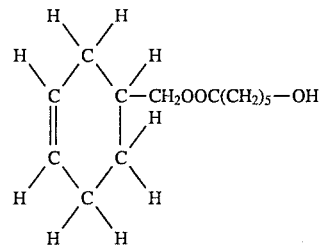

and a number average molecular weight of 226, 100 grams (1.0 mol) of methyl methacrylate, and 0.50 gram each of phenothiazine and methoxyphenol. Hexane was placed in the addition funnel. The contents of the reactor were heated to 95° C. and hexane was fed at the rate of about 2 cc/min until about 25 cc of a mixture of hexane, methyl methacrylate, and water were collected overhead at a head temperature of 65°–70° C. The reaction mass was cooled to 50° C. and 0.36 gram of sodium methoxide was added. The reaction temperature was then increased to 80°–85° C. and the hexane feed was again established at 2 cc/min. The reaction was continued at this temperature for about 2.5 hours, during which time a mixture of methanol and hexane was collected at a head temperature of 50°–60° C.

The reaction product was then cooled and diluted with an equal volume of a 1:1 mixture of hexane and toluene. The resulting mixture was washed two times with 150 ml portions of cold water and then light volatiles were stripped off on a rotary evaporator at about 45°–50° C. There was a 159 gram yield of unsaturated caprolactone methacrylate of the following average structure:

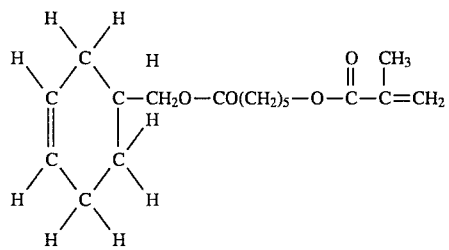

Example 7

One hundred-twenty (120) grams (0.4 mole) of an unsaturated n-caprolactone acrylate with the following average structure:

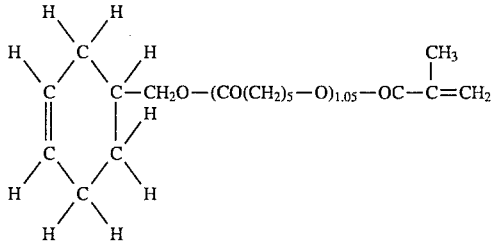

and 0.045 gram of methoxyphenol were charged to a reaction flask equipped with a thermocouple, mechanical stirrer, and addition funnel that was positioned over an ice bath and that had a heat lamp positioned so its radiation would fall on the reactants. Temperature control was achieved by raising the ice bath or turning on the heat lamp. One hundred-fifty (150) grams of a 23% solution of peracetic acid in ethyl acetate were placed in the addition funnel. The reactants were stirred and heated to 40° C. and the peracetic acid solution was slowly added to the reactor over a two-hour period while maintaining the temperature at 40° C. The mixture was stirred at 40° C. for an additional 2.5 hours, after which time analysis indicated that no additional peracetic acid was being consumed.

The epoxidized reaction product was cooled to below room temperature and diluted with 200 cc of cold toluene, washed with 130 ml portions of cold water four times, washed with 100 cc of an aqueous 1% sodium bicarbonate solution one time, and washed with 130 ml portions of cold water three additional times. Analysis for acid indicated that the residual acetic acid was 0.06%. Methoxyphenol (400 parts per million) was added to the product and volatiles were stripped off in a rotary evaporator at 35°–45° C. and a subatmospheric pressure of 2 mmHg to yield 115 grams of an epoxidized product with a number average molecular weight of 302 and the following average structure:

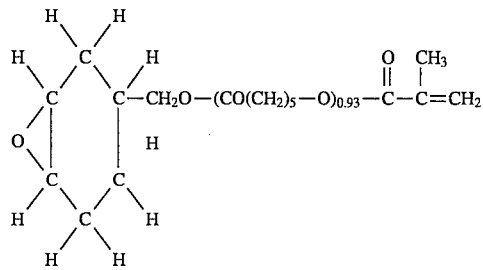

Example 8

Example 7 was repeated with one-half of the amounts of reactants indicated above to yield 55 grams of a product with a number average molecular weight of 297 and the following average structure:

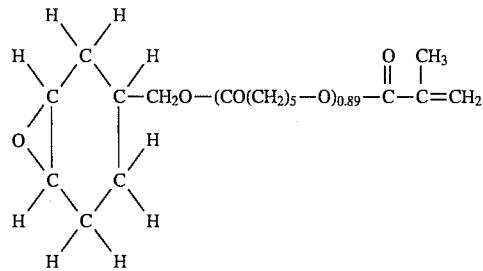

Example 9

One hundred-twenty (120) grams (0.4 mole) of an unsaturated poly-n-caprolactone acrylate with the following average structure

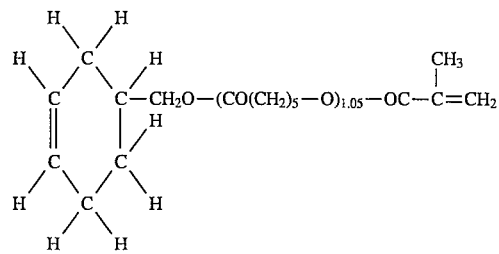

and 0.045 gram of methoxyphenol were charged to a reaction flask equipped with a thermocouple, mechanical stirrer, and addition funnel that was positioned over an ice bath and that had a heat lamp positioned so its radiation would fall on the reactants. Temperature control was achieved by raising the ice bath or turning on the heat lamp. One hundred-fifty (150) grams of a 23% solution of peracetic acid in ethyl acetate were placed in the addition funnel. The reactants were stirred and heated to 40° C. and the peracetic acid solution was slowly added to the reactor over a two-hour period while maintaining the temperature at 40° C. The mixture was stirred at 40° C. for an additional 2.5 hours, after which time analysis indicated that no additional peracetic acid was being consumed.

The epoxidized reaction product was cooled to below room temperature and then fed to a rotary evaporator. Volatiles were removed at 40° C. and 2 mmHg. The product was dissolved in 30 cc of toluene, which was then removed along with any other volatiles in the rotary evaporator at the same temperature and pressure. The resulting product was diluted with an equal volume of toluene and fed to a rotary evaporator at 70° C. and a subatmospheric pressure of 1 mmHg to remove the toluene and other volatiles. This latter dilution and evaporation was repeated. Analysis indicated a residual acetic acid content of 0.097% and a yield of epoxidized product with a number average molecular weight of 298 and the following average structure:

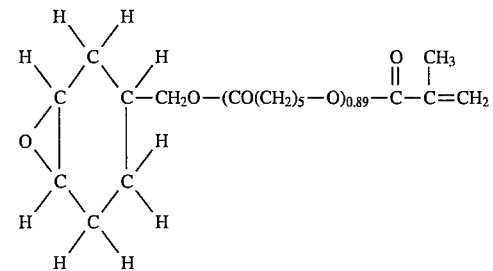

Example 10

A 12-liter, glass reactor was equipped with a heating mantle, mechanical stirrer, nitrogen purge, and a reflux/short column distillation head. Four kilograms of an unsaturated poly-e-caprolactone, with a number average molecular weight of 226 and the following average structure:

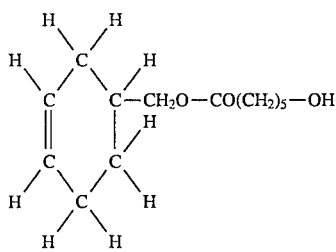

3.2 grams of methyl methacrylate, and 11.45 grams each of phenothiazine and methoxyphenol were charged to the reactor and heated to 95° C. while stirring. Hexane was then fed to the reactor at a rate of 38 cc/minute while maintaining the reactor temperature between 90° C. and 95° C. The hexane and adventitious water were collected overhead at a head temperature of 65° C. After 500 grams of the distillate were collected, the hexane feed was stopped. Analysis of the reactor contents indicated that the water content of the reactants was less than 75 parts per million.

The reactants were then cooled to 60° C. and 11.45 grams of sodium methoxide were added. The temperature was increased to 90° C. and hexane addition was re-established at 41 cc/minute. The transesterification reaction temperature was maintained at 100° C. to 105° C. and hexane, other volatiles, and a hexane/methanol azeotrope were collected overhead at a head temperature of 65° C. to 67° C. until a total of 2.7 kilograms of hexane had been fed to the reactor. The reaction was then cooled to 60° C. and the sodium methoxide catalyst was neutralized with 12.7 grams of acetic acid.

The reaction mixture was diluted with hexane until a mixture with a specific gravity of 0.9 was obtained. The mixture was then washed with 3.3 kilogram portions of water two times. The organic layer was treated with 2.7 grams of methoxyphenol and 2.1 grams of phenothiazine, and the volatile components were stripped off using a rotary evaporator with final stripping conditions of 50° C. and 1 mmHg. A yield of 4.7 kilograms of unsaturated caprolactone methacrylate product was obtained with the following average structure:

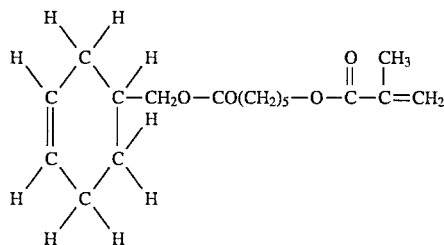

Example 11

Four and five-tenths (4.5) kilograms of the unsaturated caprolactone methacrylate product prepared in Example 10 and 200 grams of ethyl acetate were placed in the 12-liter reactor described in Example 10, with the exception than no distillation column was used. These ingredients were heated to 40° C. while stirring. Then 5.63 kilograms of a 23% solution of peracetic acid in ethyl acetate were slowly added over a two-hour period. During this addition period, the temperature was maintained between 38° C. and 42° C. and controlled by the rate of peracetic acid solution addition and by vacuum refluxing the ethyl acetate solvent. After addition of the peracetic acid solution was completed, the reaction mixture was maintained at 38°–42° C. for 105 minutes, after which time peroxide titration showed the reaction to be complete.

Ethyl acetate and some of the by-product acetic acid were removed from the reaction mixture by vacuum distillation at 40 mmHg. The resulting product mixture was then treated with 0.8 gram of phenothiazine and the remaining acetic acid was removed using a wiped film evaporator operating at 5–10 mmHg and using xylene as an azeotroping agent to yield 4.2 kilograms of e-caprolactone methacrylate 3,4-epoxycyclohexanecarboxylate product of the following average structure:

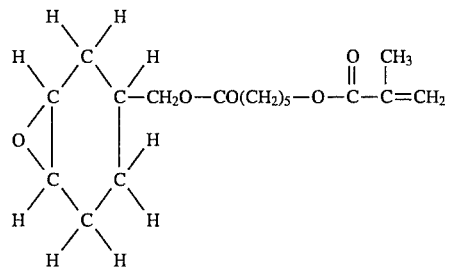

Examples 12–29

Illustrative formulations. The following ingredients are placed in a suitable container and well mixed. They are then coated onto metal panels, wood, paper, paperboard, plastic and vinyl-tile substrates with a No. 20 wire-wound rod. The coated substrates are then exposed to a 200 watt-per-inch, medium-pressure-mercury-vapor ultraviolet-light source at speeds ranging from 10 to 100 feet-per-minute. Tack-free coatings with useful properties result.

| Ingredients, g | EXAMPLE | | | |
|---|---|---|---|---|
| | 12 | 13 | 14 | 15 |
| Example 1 Product | 96.0 | 50.0 | 25.0 | 5.0 |
| Trimethylolpropane triacrylate | — | 45.0 | 52.0 | 85.0 |
| Hexanediol diacrylate | — | — | 20.0 | 6.0 |
| 2,2-diethoxyacetophenone | 4.0 | 5.0 | 3.0 | 4.0 |

| Ingredients, g | EXAMPLE | | | |
|---|---|---|---|---|
| | 16 | 17 | 18 | 19 |
| Example 2 Product | 96.0 | 30.0 | 50.0 | 25.0 |
| Example 1 Product | — | 10.0 | 46.0 | — |
| Trimethylolpropane triacrylate | — | 40.0 | — | 50.0 |
| Hexanediol diacrylate | — | 15.0 | — | 20.0 |
| 2,2-diethoxyacetophenone | 4.0 | 5.0 | 4.0 | 5.0 |

| Ingredients, g | EXAMPLE | | | |
|---|---|---|---|---|
| | 20 | 21 | 22 | 23 |
| Example 3 Product | 96.0 | 20.0 | 30.0 | 70.0 |
| Example 2 Product | — | 10.0 | — | — |
| Trimethylolpropane triacrylate | — | 50.0 | 66.0 | 20.0 |
| Hexanediol diacrylate | — | 15.0 | — | 5.0 |
| 2,2-diethoxyacetophenone | 4.0 | 5.0 | 4.0 | 5.0 |

| Ingredients, g | EXAMPLE | | | | | |
|---|---|---|---|---|---|---|
| | 24 | 25 | 26 | 27 | 28 | 29 |
| Example 2 Product | 97.0 | 48.0 | 30.0 | 10.0 | 25.0 | 40.0 |
| Example 1 Product | — | — | 10.0 | — | — | — |
| 3,4-epoxycyclohexane- | — | 50.0 | 40.0 | 70.0 | 58.0 | 37.0 |

-continued

| | | | | | | |
|---|---|---|---|---|---|---|
| methyl 3,4-epoxycyclo-hexanecarboxylate | | | | | | |
| Trimethylolpropane triacrylate | — | — | 16.0 | — | — | — |
| Polycaprolactone polyol* | — | — | — | 20.0 | — | — |
| Poly(tetramethylene oxide) polyol** | — | — | — | — | 15.0 | — |
| Propylene glycol | — | — | — | — | — | 20.0 |
| Aryl sulfonium antimony salt photoinitiator## | 3.0 | 2.0 | — | 2.5 | 2.0 | 3.0 |
| Aryl sulfonium phosphorous salt photoinitiator## | — | — | 4.0 | — | — | — |

*A 540 average molecular weight trifunctional polycaprolactone polyol marketed by Union Carbide Corporation under the tradename TONE ™ 0305.
**A 1000 average molecular weight, difunctional poly(tetramethylene oxide) polyol marketed by Quaker Chemical as Polymeg ™ 1000.
CYRACURE ™ UVI-6974, a hexafluoroantimonate aryl sulfonium salt marketed by Union Carbide Corporation.
CYRACURE ™ UVI-6990, a hexafluorophosphate aryl sulfonium salt marketed by Union Carbide Corporation.

Example 30

One mole of the product of Example 1, 1 mole of styrene, one mole of butyl acrylate, 10 grams of VAZO 52 (azo-based polymerization initiator sold by Du Pont), and 200 grams of methyl isobutyl ketone are placed in a glass reactor equipped with a stirrer, temperature measuring device, and a nitrogen inlet and outlet, and a water-cooled condenser. The mixture is heated to reflux (about 115° C.) and maintained at this temperature for 30 minutes, and then the temperature is decreased to 80° C. and held at this temperature for two hours. The product is cooled to room temperature and stored for future use.

Example 31

The product of Example 30 is converted into a polyepoxide product by reaction with peracetic acid by the same method as used in Example 2. The polyepoxide is useful in photocured or thermally cured coatings, inks, photoresists, and adhesives when formulated with suitable photoinitiators and/or catalysts. Flexibilized products are obtained by formulating polyols with the product of Example 30 and curing in the manner described.

Example 32

One-half mole of the product of Example 2, 1 mole of styrene, one mole of t-butyl acrylate, 0.1 mole of hydroxyethyl acrylate, 10 grams of VAZO 52 (azo-based polymerization initiator sold by DuPont), and 200 grams of methyl isobutyl ketone are placed in a glass reactor equipped with a stirrer, temperature measuring device, and a nitrogen inlet and outlet, and a water-cooled condenser. The mixture is heated to reflux (about 115° C.) and maintained at this temperature for 30 minutes, and then the temperature is decreased to 80° C. and held at this temperature for two hours. The resulting product is cooled to room temperature and stored for future use.

Example 33

Under ultraviolet light-free conditions, the product of Example 32 is formulated with an onium salt photoinitiator, the solvent is removed by spray drying, and the resulting product is used as a powder coating by electrostatically spraying it onto a substrate and heating to melt the powder and then subjecting the film to ultraviolet light. If desired, the spray dried powder may be fluid energy milled to improved its solid-state flow characteristics.

What is claimed is:

1. An unsaturated polylactone acrylate of the formula:

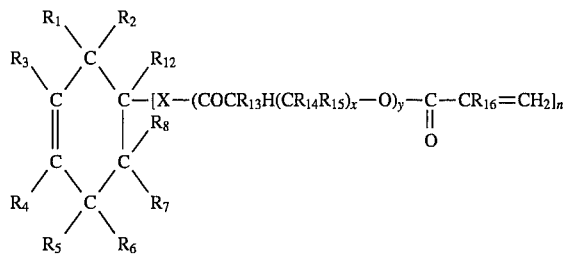

wherein $R_1$ to $R_8$ are the same or different and are hydrogen, phenyl, or unsubstituted or substituted alkyl groups of 1 to about 8 carbon atoms, n has a value of one or two, $R_{12}$ is hydrogen when n is one and does not exist when n is two, $R_{13}$, $R_{14}$, and $R_{15}$ are the same or different and are hydrogen, phenyl, cyclohexyl, linear or branched alkyl groups of up to about 8 carbon atoms, or halogen with the proviso that not more than three of the $R_{13}$ to $R_{15}$ are alkyl, phenyl, cyclohexyl, or halogen groups, $R_{16}$ is hydrogen, methyl, or ethyl, x is an integer of one to about 6, and y is up to about 50, X is $CH_2O$ when n is equal to two and is $CH_2O$ or $COOCH_2CHR_{17}O$ when n is equal to one, and $R_{17}$ is either hydrogen or methyl.

2. A unsaturated polylactone acrylate as in claim 1 wherein y is up to about 10.

3. A unsaturated polylactone acrylate as in claim 1 wherein y is up to about 4.

4. An unsaturated polylactone acrylate as in claim 1 wherein $R_1$ to $R_8$ are hydrogen.

5. An unsaturated polylactone acrylate as in claim 4 wherein x is from 3 to 5.

6. An unsaturated polylactone acrylate as in claim 5 wherein $R_{13}$ is hydrogen and one $R_{14}$ or $R_{15}$ is methyl.

7. An unsaturated polylactone acrylate as in claim 5 wherein $R_{13}$ is hydrogen and two of $R_{14}$ and/or $R_{15}$ are methyl.

8. An unsaturated polylactone acrylate as in claim 5 wherein $R_{13}$ to $R_{15}$ are hydrogen.

9. An unsaturated polylactone acrylate as in claim 1 wherein $R_1$, $R_2$, and $R_4$ to $R_8$ are hydrogen and $R_3$ is methyl.

10. An unsaturated polylactone acrylate as in claim 1 wherein $R_1$ to $R_3$ and $R_5$ to $R_8$ are hydrogen and $R_4$ is methyl.

11. An unsaturated polylactone as in claim 8 wherein X is $CH_2O$ and n is one.

12. An unsaturated polylactone as in claim 8 wherein X is $CH_2O$ and n is two.

13. An unsaturated polylactone as in claim 8 wherein X is $COOCH_2CHR_{17}O$ and n is one.

14. An unsaturated polylactone as in claim 13 wherein $R_{17}$ is hydrogen.

15. An unsaturated polylactone as in claim 13 wherein $R_{17}$ is methyl.

16. An unsaturated polylactone acrylate as in claim 4 wherein y is about one.

17. A curable composition comprising an unsaturated polylactone acrylate of claim 1 and an initiator.

18. A curable composition as in claim 17 where the initiator is thermally activated.

19. A curable composition as in claim 17 wherein the initiator is activated by light or radiation.

* * * * *